(12) United States Patent
Gangl

(10) Patent No.: US 8,584,537 B2
(45) Date of Patent: Nov. 19, 2013

(54) EXTRACTION TUBE FOR EMISSION MEASUREMENT SYSTEMS

(75) Inventor: George Gangl, Gratkorn (AT)

(73) Assignee: AVL List GmbH, Graz (AT)

( * ) Notice: Subject to any disclaimer, the term of this patent is extended or adjusted under 35 U.S.C. 154(b) by 0 days.

(21) Appl. No.: 13/137,891

(22) Filed: Sep. 20, 2011

(65) Prior Publication Data

US 2012/0073540 A1 Mar. 29, 2012

(30) Foreign Application Priority Data

Sep. 23, 2010 (AT) ................ A 1590/2010

(51) Int. Cl.
*G01N 1/22* (2006.01)
(52) U.S. Cl.
USPC ....................................... 73/863.81

(58) Field of Classification Search
None
See application file for complete search history.

(56) References Cited

U.S. PATENT DOCUMENTS

| | | | | |
|---|---|---|---|---|
| 5,090,258 | A | * | 2/1992 | Yamasaki et al. .......... 73/863.03 |
| 5,241,867 | A | * | 9/1993 | Cohen et al. ............... 73/863.41 |
| 5,907,109 | A | * | 5/1999 | Tedeschi .................... 73/864.73 |
| 6,490,937 | B2 | * | 12/2002 | Hanashiro et al. ......... 73/863.11 |
| 6,976,397 | B2 | * | 12/2005 | Widmer ..................... 73/863.03 |
| 2009/0178494 | A1 | * | 7/2009 | Liu et al. .................... 73/863.31 |

* cited by examiner

*Primary Examiner* — Robert R Raevis
(74) *Attorney, Agent, or Firm* — Dykema Gossett PLLC

(57) ABSTRACT

An extraction tube for exhaust gas emission measurement systems of internal combustion engines includes at least two tubes which extend in parallel over a portion of the length of the extraction tube, and wherein each tube includes an exhaust gas extraction point to which a sampling line can be connected.

8 Claims, 1 Drawing Sheet

EXTRACTION TUBE FOR EMISSION MEASUREMENT SYSTEMS

BACKGROUND OF THE INVENTION

1. Field of the Invention

The invention relates to an extraction tube for emission measurement systems for exhaust gas of internal combustion engines, the extraction tube having at least two exhaust gas extraction points and connecting pieces to at least two sampling lines, and to an emission measurement system for exhaust gas of internal combustion engines, including at least one analysis and evaluation device for the exhaust gas of internal combustion engines, comprising at least one analysis and evaluation device for the exhaust gas as well as a plurality of sampling lines from the exhaust gas system of the internal combustion engine to the or each analysis and evaluation device.

2. The Prior Art

For mobile applications as well as on test stands, emission measurement systems are used in case a plurality of components in the exhaust gas of an internal combustion engine are to be analyzed. For this purpose, a plurality of analysis devices and often also a plurality of sampling lines and exhaust gas extraction points are provided in the exhaust gas system of the internal combustion engine.

Currently, the lengths of exhaust pipes, in particular in case of heavy duty engines, have to be manufactured according to the number of exhaust gas extraction points. If four or more extraction points are needed, the space, in particular in case of test stands, is not sufficient for a straight tube so that additional bends have to be installed which, however, can no longer be used for other test arrangements.

It was therefore the object of the present invention to propose an extraction tube which, with little required space, in particular with a short overall length, and little constructional efforts, allows multiple sampling from the exhaust gas of internal combustion engines, and which is not specifically designed for one special application.

SUMMARY OF THE INVENTION

In order to achieve this object, an extraction tube as described above is characterized according to the invention in that over a portion of the length of the extraction tube at least two tubes run parallel to each other, wherein each tube is provided with an exhaust gas extraction point. Such a tube can be used in a versatile way on most of the test stands, also in small test cells, and as a standardized module with connection ports for the measuring probes and with clamping ring, and it can be used multiple times.

According to an advantageous exemplary embodiment of the invention, the extraction tube is characterized in that the total cross-section of all tubes is equal to the cross-section of the preceding section of the extraction tube. The length of an exhaust pipe for an exhaust pipe having a diameter of 10 cm thus can be reduced from three meters to slightly more than one meter, even in case of a plurality of extraction points.

Advantageously, for maintaining a laminar flow in the region of the sampling points it can be provided that the length of the extraction tube corresponds to at least the nine-fold diameter of the tubes, wherein one length of at least the six-fold diameter of the tubes is provided upstream of the first exhaust gas extraction point and one length of at least the three-fold diameter of the tubes is provided downstream of the last exhaust gas extraction point.

For setting a uniform distribution of the exhaust gas flow of the internal combustion engine for all sampling points, such an embodiment can be particularly advantageous in which flow guiding devices are provided which distribute the exhaust gas flow uniformly between all present tubes.

In this embodiment, a particularly effective design provides that a substantially conical portion is arranged upstream of the beginning of the tubes.

For achieving the given object, an emission measurement system as described above is characterized by an extraction tube connectable to the exhaust gas system of the internal combustion engine according to any one of the preceding paragraphs.

In the following description, the invention is to be described in more detail by means of the attached drawings of a specific but not limiting exemplary embodiment.

DETAILED DESCRIPTION OF THE PREFERRED EMBODIMENT

Figure 1:
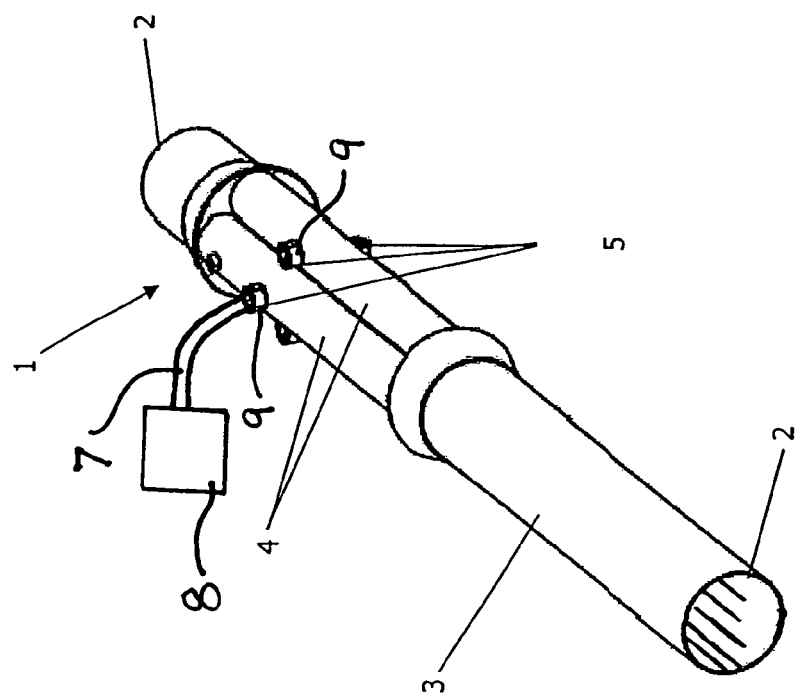
FIG. 1 shows a perspective view of an extraction tube according to the invention.

The extraction tube 1 for emission measurement systems for the exhaust gas of internal combustion engines shown in FIG. 1 can be inserted in an exchangeable and thus reusable manner, for example by means of connecting flanges provided at the ends 2, between the exhaust gas system of the internal combustion engine and the exhaust gas system, for example, of a test stand. Adjacent to a substantially straight tube section 3, a coaxial longitudinal section is provided downstream in the flow direction in which section, for example, four tubes 4 run parallel to each other which are again substantially straight. Each of the tubes 4 is provided with an exhaust gas extraction point 5 with a connecting flange 9 for sampling lines via which the extracted partial exhaust gas flows can be fed to an analysis and evaluation unit 8 of the emission measurement system for the examined internal combustion engine.

By guiding a plurality of exhaust gas flows in parallel in the tubes 4, the extraction tube 1, despite the straight embodiment, requires only a small installation space for multiple samplings so that it can be used in a versatile way and even multiple times on most of the test stands and also in small test cells and as a standardized module.

The tubes 4 are preferably dimensioned in such a manner that the total cross-section of all tubes 4 is equal to the cross-section of the preceding section 3 of the extraction tube 1. Each of the tubes preferably has a diameter that corresponds to the root of the square of the diameter of the preceding section 3 which first is to be divided by the number of the existing tubes 4. At an initial diameter of 10 cm, the length of the extraction tube 1 can be reduced from approximately three meters to slightly more than one meter, even if a plurality of extraction points is provided, wherein then each of the four tubes 4 has a diameter of 5 cm.

In order to maintain laminar flow in the region of the sampling points 5, the length of each tube 4 should correspond to at least the nine-fold diameter of the tubes 4, wherein the sampling points 5 are preferably provided in that half of the tube 4 which is farther away from the section 3. In any case, one length of at least the six-fold diameter of the respective associated tube 4 should lie upstream of the exhaust gas extraction point 5 and, preferably, one length of at least the three-fold diameter of the respective associated tube 4 should lie downstream of the last exhaust gas extraction point 5.

Figure 2A:
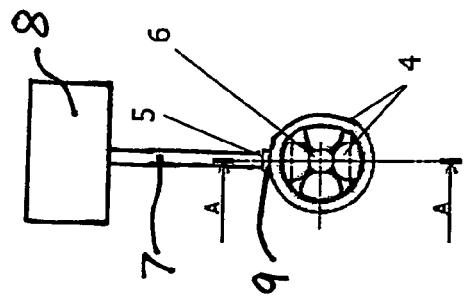
FIG. 2a is a longitudinal section through the extraction tube of FIG. 1 as seen along line 2a-2a in FIG. 2b.
Figure 2B:
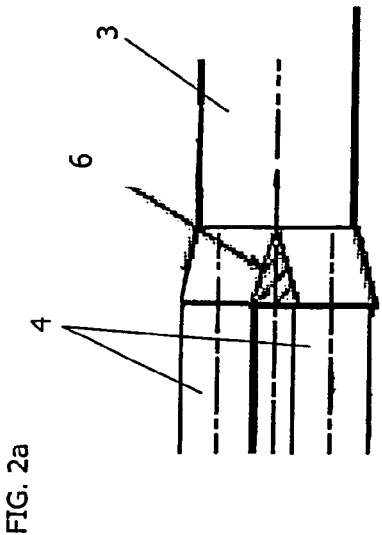
FIG. 2b shows a cross-section through the extraction tube in the region of the distribution between four individual tubes.

For setting a distribution of the exhaust gas flow of the internal combustion engine which is uniform for all sampling points 5, a flow guiding device 6 is used which is illustrated in FIGS. 2a and 2b in more detail and which, in the illustrated exemplary embodiment, is arranged as a substantially conical portion upstream and before the beginning of the tubes 4 (see FIG. 2a). Through this device 6, the exhaust gas flow is uniformly distributed between all existing tubes 4.

The invention claimed is:

1. An extraction device for exhaust gas emission measurement systems, said extraction device comprising:
   first tube having an upstream end and a downstream end, and
   a plurality of parallel second tubes having respective upstream and downstream ends, said upstream ends of said plurality of second tubes being in communication with said downstream end of said first tube such that exhaust gas flow in the first tube is distributed between all of said second tubes, each of said second tubes having a respective discharge opening in a side wall thereof between respective upstream and downstream ends thereof and a connecting nipple on an outer surface thereof so as to surround a respective discharge opening for attachment of a sampling line.

2. The extraction device according to claim 1, wherein said first tube is rectilinear and said second tubes are collinear with said first tube.

3. The extraction device according to claim 1, including an internal flow-guiding device upstream of said upstream ends of said second tubes for uniformly distributing the exhaust gas from said first tube into said second tubes.

4. The extraction device according to claim 3, wherein said flow-guiding device comprises an essentially conical element.

5. The extraction device according to claim 1, wherein a total cross-section of said plurality of second tubes is equal to a cross-section of said first tube.

6. The extraction device according to claim 1, wherein a length of each of said plurality of second tubes is equal to at least a nine-fold diameter of the respective second tube.

7. The extraction device according to claim 6, wherein in at least one of said plurality of second tubes the respective discharge opening is located such that one length of at least the six-fold diameter extends upstream of a first discharge opening of said at least one of said plurality of second tubes and one length of at least the three-fold diameter extends downstream of a last discharge opening of said at least one of said plurality of second tubes.

8. An exhaust gas emission measurement system for an internal combustion engine, comprising:
   an analysis and evaluation device,
   an extraction device which includes a first tube having an upstream end and a downstream end, a plurality of parallel second tubes having respective upstream and downstream ends, said upstream ends of said plurality of second tubes being in communication with said downstream end of said first tube so that each of said plurality of second tubes receives a distribution of all the exhaust gas passing from said first tube, each of said second tubes having a respective discharge opening in a side wall thereof between said upstream and downstream ends thereof and a connecting nipple on an outer surface thereof so as to surround a respective discharge opening, and
   at least one sampling line which extends between said analysis and evaluation device and at least one of said connecting nipples surrounding a discharge opening.

* * * * *